United States Patent [19]

Taoka et al.

[11] 4,275,158

[45] Jun. 23, 1981

[54] MANUFACTURE OF FATTY ACIDS HAVING STRAIGHT AND LONG CARBON CHAINS USING A MICROORGANISM

[75] Inventors: Akira Taoka; Seiichi Uchida, both of Urawa, Japan

[73] Assignee: Bio Research Center Company, Ltd., Saitama, Japan

[21] Appl. No.: 110,411

[22] Filed: Jan. 7, 1980

[51] Int. Cl.³ .................................................. C12P 7/40
[52] U.S. Cl. ................................... 435/136; 435/142; 435/249; 435/255; 435/822
[58] Field of Search ............... 435/136, 142, 249, 255, 435/822, 911

[56] References Cited

U.S. PATENT DOCUMENTS

| | | | |
|---|---|---|---|
| 3,080,296 | 3/1963 | Robbins | 435/142 |
| 3,843,466 | 10/1974 | Akabori et al. | 435/142 |
| 3,912,586 | 10/1975 | Kaneyuki et al. | 435/142 X |

OTHER PUBLICATIONS

Van der Linden et al. "Mechanisms of Microbial oxidations of petroleum hydrocarbons" Advances in Enzymology, vol. 27, pp. 469-502, Interscience (1965).

*Primary Examiner*—R. B. Penland
*Attorney, Agent, or Firm*—Donald R. Cassady

[57] ABSTRACT

A method for the oxidation of hydrocarbons to monocarboxylic acids and then to dicarboxylic acids by the aerobic cultivation or resting cell reaction of the organism *Debaryomyces vanriji* (BR-308) ATCC 20588.

4 Claims, No Drawings

MANUFACTURE OF FATTY ACIDS HAVING STRAIGHT AND LONG CARBON CHAINS USING A MICROORGANISM

BACKGROUND OF THE INVENTION

This invention concerns the production of dicarboxylic acids or dicarboxylic acids along with monocarboxylic acids corresponding to hydrocarbons having straight and long carbon chains and/or monocarboxylic acids having straight and long carbon chains as substrate using a microorganism.

Monocarboxylic acids having straight and long carbon chains are useful raw materials of surfactants, detergents, stabilizers, and the like. However, their use has been limited since natural fats, such as beef fat and palm oil, have been mostly employed for the preparation of the above mentioned chemicals.

Dicarboxylic acids having straight and long carbon chains are useful raw materials for the preparation of plasticizers, synthetic resins, synthetic lubricants, oils, perfumes, and the like. The establishment of a method of the manufacture of dicarboxylic acids with varied carbon numbers on an industrial scale from petroleum derived feedstocks has been desired.

Microbial production of monocarboxylic acids and dicarboxylic acids is well known. In these reported reactions, normal paraffins contained in petroleum distillate are used as substrate for corresponding mono- and di-carboxylic acids. Further, the use of natural as well as synthetic monocarboxylic acids as raw materials for microbial conversion to dicarboxylic acids has been reported: VanderLinden and Thijsse, "The Mechanisms of Microbial Oxidations of Petroleum Hydrocarbons"; Advances in Enzymology, Vol. 27, p. 469 (1965); Y. Minura, U.S. Pat. No. 3,793,153; S. Akabori, et al., U.S. Pat. No. 3,843,466.

Commercially advantageous methods have not yet been established.

SUMMARY OF THE INVENTION

It has now been found that a yeast strain which belongs to Debaryomyces genus can produce dicarboxylic acids or dicarboxylic acids along with monocarboxylic acids by oxidizing hydrocarbons or mixtures of hydrocarbons and moncarboxylic acids having straight and long carbon chains.

As described herein, this invention is characterized by using a yeast strain belonging to the Debaryomyces genus, *Debaryomyces vanriji*; in order to produce dicarboxylic acids or dicarboxylic acids along with monocarboxylic acids advantageously.

Utilizing this microorganism, this invention produces, (1) dicarboxylic acids or a mixture of dicarboxylic acids and monocarboxylic acids corresponding to the hydrocarbons having straight and long carbon chains which have been used as the substrate, (2) dicarboxylic acids corresponding to natural as well as synthetic monocarboxylic acids used as raw material and (3) dicarboxylic acids corresponding to a mixture of hydrocarbons having long, straight carbon chains and monocarboxylic acids of similar chain length when used as substrate.

DETAILED DESCRIPTION OF THE INVENTION

The carboxylic acid producing microorganism, *Debaryomyces vanriji*(BR-308), employed in this invention was collected from the soil near a petroleum refinery in Akita Prefecture and was isolated for use. Said microorganism was identified as *Debaryomyces vanriji* from the following micrological properties. The strain has been deposited with the American Type Culture Collection with the accession number ATCC 20588.

The properties of said microorganism are described below:

1. Shape and size:
   Growth in malt extract: After 3 days at 25° C. the cells are spherical to oval, (3–8)×(4–20)u; single or in groups. A sediment and a thin, dull, creeping pellicle are formed.
   Growth on malt agar: After 7 days at 25° C. the colony is whitish or dark yellowish, dull to shiny, smooth with slightly sinuous margin.
   Slide Culture on potato—and corn meal agar: A primitive pseudomycelium is abundantly formed.
2. Formation of ascospores:
   Ascospores are formed on ⅛ M Van't Hoff's gypsum blocks and V 8 agar. The spore are spherical or oval.
3. Fermentation of sugars: Negative.
4. Assimilation of carbon compounds: See Table 1.
5. Splitting of arbutin: Positive.
6. Assimilation of $KNO_3$: Negative.
7. Growth in vitamin-free medium: Positive.
8. Growth at 37° C.: Positive.

TABLE 1

| Assimilation of carbon compounds | |
|---|---|
| Glucose | + |
| Galactose | + |
| L-sorbose | + |
| Sucrose | + |
| Maltose | + |
| Cellobiose | + |
| Trehalose | + |
| Lactose | − |
| Melibiose | + |
| Soluble Starch | + |
| D-xylose | + |
| Ethanol | + |
| Glycerol | + |
| Salicin | + |
| Inositol | − |

In this invention, hydrocarbons having 10 to 18 carbon atoms are appropriate raw materials (substrate) for the production of dicarboxylic acids or a mixture of di- and monocarboxylic acids especially hydrocarbons of 11 to 16 carbon chain length are desirable. For the selective production of dicarboxylic acids, monocarboxylic acids and hydrocarbons having a skeletal length of 10 to 18 carbon atoms each are suitable precursors, hydrocarbon skeletal lengths of 11 to 16 carbon numbers are preferred.

The oxidation reaction of this invention is a typical resting cell phenomenon and can be carried out in an aqueous buffer solution, as for example a phosphate buffer solution of pH 7.

The reaction can also be carried out in a growth medium which contains nutrient for the yeast. The reaction then becomes a cultivation-oxidation reaction. In this mode of operation, the media shall contain the usual nutrient material including an assimilable carbon source, nitrogen source, and appropriate vitamins and minerals, all well-known to those skilled in the art.

Carbon sources appropriate to a growth medium can include for example glucose, sucrose, maltose, the substrate hydrocarbon or monocarboxylic acid, and the like.

Nitrogen sources can include inorganic nitrogen compounds as for example ammonium nitrate, ammonium phosphate, or the like; and organic nitrogen-containing materials as for example peptone, corn steep liquor, and amino acids.

Vitamins and minerals needed for growth can include sodium phosphate, calcium phosphate, magnesium sulfate, zinc sulfate, ferrous sulfate, manganese sulfate as minerals and yeast extract and the like as vitamin-containing additive.

When the oxidation is carried out as a resting cell reaction, it becomes necessary to grow up a healthy cell mass prior to oxidation. This cell mass is best prepared by growing the yeast culture in the above growth medium prior to oxidation. The whole cell culture including cells and nutrient material can be used in the oxidation reaction, or the cell mass can be removed from the spent nutrient by centrifugation or filtration prior to adding the cell mass to the substrate.

Thus, in this invention, the strain of carboxylic acid producing microorganisms, Debaryomyces vanriji(BR-308) ATCC 20588, or a culture thereof or cells of the strain cultured previously are added to the medium containing the substrate to carry out the reaction and agitated, aerated through a nozzle, or shaken so that the microorganism can contact the components of the medium thoroughly.

The reaction temperature is kept at 25° to 35° C. and pH is controlled at 3 to 9, preferably pH 4 to 8. The period of time of reaction depends on the substrate to be used, but usually a reaction takes 24 to 120 hours to finish completely.

We have found it advantageous to use a mixed substrate containing at least some monocarboxylic acid for the reason that the monocarboxylic acid tends to increase solubility of the substrate in the aqueous reaction mixture and to suppress accumulation of additional monocarboxylic acid during oxidation.

A readily available source of the monocarboxylic acid for this mixed substrate is from the accumulation of the acid from previous reactions.

When cultivation (reaction) is carried out as described above, the substantial amount of dicarboxylic acids or a mixture of dicarboxylic acids containing monocarboxylic acids is produced and accumulated. These carboxylic acids are separated and purified by a conventional method such as extraction, solid-liquid separation, neutralization-extraction and fractional distillation, and then harvested as monocarboxylic acids and dicarboxylic acids, or a mixture of both.

As illustrated by the preferred embodiment described below, the organism of this invention produces monocarboxylic acids and dicarboxylic acids in high yields by well known cultivation methods using the new microorganism. Therefore, it is believed that this invention contributes greatly to the production or carboxylic acids with straight and long carbon chains.

EXAMPLE 1

Medium composition for flask cultivation
Sucrose: 30 g
NH$_4$Cl: 4 g
KH$_2$PO$_4$: 2 g
MgSO$_4$.7H$_2$O: 0.6 g
ZnSO$_4$.7H$_2$O: 0.01 g
FeSO$_4$.7H$_2$O: 0.01 g
Mycological peptone: 0.5 g
Yeast extract: 0.5 g The components for pre-cultivation were dissolved in distilled water to make the total volume 1 liter and adjusted to pH 6.5. One hundred milliliters of the resulting media was added to a 500 ml flask and sterilized in an autoclave at 121° C. for 15 minutes. Cells of Debaryomyces vanriji(BR-308) ATCC 20588 which had been grown on malt extract agar at 30° C. for one month were inoculated (3 loopsful) to the above sterile medium and were cultured on a reciprocal shaker at 30° C. for 29 hours.

Medium composition for fermentation
KH$_2$PO$_4$: 10 g
NH$_4$Cl: 5 g
MgSO$_4$.7H$_2$O: 0.6 g
FeSO$_4$.7H$_2$O: 0.01 g
ZnSO$_4$.7H$_2$O: 0.008 g
Mycological peptone: 0.5 g
Yeast Extract: 0.5 g The above-enumerated components for a fermentation medium were dissolved into distilled water to make the total volume 1 liter and sterilized at 121° C. for 15 minutes; 800 ml of the medium and 110 g of the appropriate hydrocarbons or carboxylic acids as shown in Table 2 were sterilized in an autoclave at 115° C. for 15 minutes.

Into a 2 l fermentor were placed 100 ml of the precultivation medium, 800 ml of the fermentation medium and 110 g of sterilized reactant substrate. The mixture was allowed to reach with aeration and agitation at 30° C. for 96 to 120 hours at pH 6.5 to pH 7.5. 2 N potassium hydroxide was used for pH adjustment. When foaming was observed during the cultivation, small quantities of a solution of 15% defoaming agent (manufactured by Toshiba Silicone Co.; TSA 730) which had previously been autoclaved at 115° C. for 15 minutes were poured into the culture medium. On finishing cultivation, solid potassium hydroxide was added to the culture broth to pH 10, the broth emptied from the fermentor, filtered under the reduced pressure using filter aid, and washed. Products were extracted by ether, methylated with diazomethane after the ether was removed and analyzed by gas chromatography.

The results are shown in Table 2.

TABLE 2

| | Concentration of acids in the medium after 96–120 hours cultivation (mg/L) | | |
|---|---|---|---|
| Substrate | Monocarboxylic Acids | Dicarboxylic Acids | |
| n-Decane | Capric Acid | 6.0 | 1,8-Octane DCA | 4.1 |
| n-Undecane | Undecyl Acid | 10.7 | 1,9-Nonane DCA | 9.1 |
| n-Dodecane | Lauric Acid | 11.3 | 1,10-Decane DCA | 16.0 |
| n-Tridecane | Tridecyl Acid | 19.1 | 1,11-Undecane DCA | 13.9 |
| n-Tetradecane | Myristic Acid | 24.5 | 1,12-Dodecane DCA | 12.8 |
| n-Pentadodecane | Pentadecyl Acid | 18.4 | 1,13-Tridecane DCA | 14.8 |
| n-Hexadecane | Palmitic Acid | 19.1 | 1,14-Tetradecane DCA | 18.3 |
| Pelargonic Acid (C$_8$H$_{17}$COOH) | | | 1,7-Pentan DCA | 6.3 |
| Lauric Acid (C$_{11}$H$_{23}$COOH) | | | 1,10-Decane DCA | 5.3 |
| Palmitic Acid (C$_{15}$H$_{31}$COOH) | | | 1,14-Tetradecane DCA | 17.3 |
| A mixture of | | | 1,10-Decane DCA | 18.0 |

TABLE 2-continued

| Substrate | Concentration of acids in the medium after 96-120 hours cultivation (mg/L) | |
|---|---|---|
| | Monocarboxylic Acids | Dicarboxylic Acids |
| n-Tridecane and Lauric Acid containing equal wt. | | |

EXAMPLE 2

Components for the fermentation medium described in Example 1 as well as 50 g sucrose were dissolved in 1 liter distilled water and adjusted to pH 5.5. Fifty milliliters of the medium were placed in a 500 ml shaking flask and inoculated with 2 loopsful of the *Debaryomyces vanriji* strain used in Example 1, and growth was maintained at 30° C. for 26 hours. The obtained culture broth was centrifuged in order to separate the cells (about 1 g dry weight). A reaction solution was prepared by mixing 100 ml of 0.5 M phosphate buffer (pH 7.0) with 10 ml of normal dodecane. A reaction was carried out between this reaction solution and the filtered cells at 30° C. for 72 hours. The reaction products were basified to pH 10 with potassium hydroxide and were analyzed using the same process as in Example 1. As a result, 4.8 mg/L of lauric acid and 3.7 mg/L of 1,10-decane dicarboxylic acids were produced in the reaction medium. For this experiment, the medium, substrate, and the equipment were autoclaved previously so that the experiment could be carried out under sterile conditions.

We claim:

1. In the production of mono- and di-carboxylic acids of the same carbon skeletal length from straight chain $C_{10}$-$C_{18}$ hydrocarbons by aerobically cultivating the hydrocarbons with a microorganism in a nutrient medium, at 25°-35° C. and pH 3-9 for 24 to 120 hours, the improvement which comprises using as the microorganism *Debaryomyces vanriji* (BR-308), ATCC 20588.

2. In the production of $C_{10}$-$C_{18}$ dicarboxylic acids of the same skeletal length from monocarboxylic acids by aerobically cultivating the monocarboxylic acid with a microorganism in a nutrient medium, at 25°-35° C. and pH 3-9 for 24 to 120 hours, the improvement which comprises using the microorganism *Debaryomyces vanriji,* (BR-308), ATCC 20588.

3. In the production of dicarboxylic acids of the same carbon skeletal length from straight chain $C_{10}$-$C_{18}$ hydrocarbons and monocarboxylic acids by aerobically cultivating the hydrocarbon and the monocarboxylic acid with a microorganism in a nutrient medium, at 25°-35° C. and pH 3-9 for 24 to 120 hours, the improvement which comprises using at the microorganism *Debaryomyces vanriji,* (BR-308), ATCC 20588.

4. In the production of mono- and di-carboxylic acids of the same carbon skeletal length from straight chain $C_{10}$-$C_{18}$ hydrocarbons by growing a microorganism in a nutrient medium, at 25°-35° C. and pH 3-9 for 24 to 120 hours, separating the cell mass comprising the microorganism and allowing the cell mass to react aerobically with the hydrocarbon, the improvement which comprises using the microorganism *Debaryomyces vanriji,* (BR-308), ATCC 20588.

* * * * *